United States Patent
Tommy et al.

(10) Patent No.: US 11,250,310 B2
(45) Date of Patent: Feb. 15, 2022

(54) ELECTRONIC SENSING SYSTEMS AND METHODS THEREOF

(71) Applicant: Tata Consultancy Services Limited, Mumbai (IN)

(72) Inventors: Robin Tommy, Trivandrum (IN); Rohan Chandrakant Vardekar, Trivandrum (IN); Rishin Raj, Trivandrum (IN)

(73) Assignee: Tata Consultancy Services Limited, Mumbai (IN)

( * ) Notice: Subject to any disclaimer, the term of this patent is extended or adjusted under 35 U.S.C. 154(b) by 1045 days.

(21) Appl. No.: 15/646,827

(22) Filed: Jul. 11, 2017

(65) Prior Publication Data
US 2018/0260686 A1    Sep. 13, 2018

(30) Foreign Application Priority Data
Mar. 9, 2017 (IN) .............................. 201721008355

(51) Int. Cl.
 *G06N 3/04* (2006.01)
 *G06N 3/08* (2006.01)
 *G01N 33/00* (2006.01)

(52) U.S. Cl.
 CPC ....... *G06N 3/0427* (2013.01); *G01N 33/0001* (2013.01); *G06N 3/08* (2013.01)

(58) Field of Classification Search
 CPC .......... G06N 3/02; G06N 3/0427; G06N 3/08; G01N 33/0001
 See application file for complete search history.

(56) References Cited

U.S. PATENT DOCUMENTS

| | | | |
|---|---|---|---|
| 8,880,448 B2 * | 11/2014 | Haddad | G01N 33/0034 706/20 |
| 2004/0186692 A1 | 9/2004 | Hengerer | |
| 2006/0191319 A1 * | 8/2006 | Kurup | G01N 33/24 73/23.34 |

(Continued)

OTHER PUBLICATIONS

Pan, Early detection and classification of pathogenic fungal disease in post-harvest strawberry fruit by electronic nose and gas chromatography—mass spectrometry (Year: 2014).*

*Primary Examiner* — Abdullah Al Kawsar
*Assistant Examiner* — Tewodros E Mengistu
(74) *Attorney, Agent, or Firm* — Finnegan, Henderson, Farabow, Garrett & Dunner, LLP (57) ABSTRACT

Electronic sensing systems and methods are disclosed. The electronic sensing system (ESS) receive an olfactory product and one or more smell characteristics of the olfactory product are detected and extracted by identifying a headspace of the olfactory product. A comparison of the extracted smell characteristics with one or more smell characteristics associated with a historic training data stored in a database is performed and a match between the extracted smell characteristics and the one or more smell characteristics associated with the historic training data is determined using machine learning technique(s). Further, the ESS generates a report for the olfactory product comprising at least one of type of the consumable, name of the olfactory product, a status of the olfactory product, an age of the olfactory product, and a decaying index, and classifies the olfactory product into one or more categories based on the report and/or the historic training data.

15 Claims, 5 Drawing Sheets

(56) References Cited

U.S. PATENT DOCUMENTS

2014/0096590 A1   4/2014  Amin et al.
2014/0221269 A1*  8/2014  Sobel .................. C11B 9/02
                                              512/5

* cited by examiner

Category: Non Vegetarian
Food Status: Spoiled
Item Name: Chicken
Number of days old: 2
Consumable: No/Not consumable
Decaying Index: 46.4

FIG. 5

ELECTRONIC SENSING SYSTEMS AND METHODS THEREOF

PRIORITY CLAIM

This U.S. patent application claims priority under 35 U.S.C. § 119 to: India Application No. 201721008355, filed on Mar. 9, 2017. The entire contents of the aforementioned application are incorporated herein by reference.

TECHNICAL FIELD

This disclosure herein generally relate to sensing systems, and, more particularly, to electronic sensing systems and methods for sensing and classifying olfactory products.

BACKGROUND

"Electronic sensing" refers to the capability of reproducing human senses using sensor arrays. Research has been conducted to develop technologies, commonly referred to as electronic noses, which could detect and recognize odors and flavors. The stages of the recognition process are similar to human olfaction and are performed for identification, comparison, quantification and other applications, including data storage and retrieval. However, hedonic evaluation is a specificity of the human nose given that it is related to subjective opinions. These sensing devices have undergone much development and are now used to fulfill industrial needs. However, results from such sensing devices are not quantitative, remain unstable and continue to produce erroneous outputs.

SUMMARY

Embodiments of the present disclosure present technological improvements as solutions to one or more of the above-mentioned technical problems recognized by the inventors in conventional systems. For example, in one embodiment, a processor implemented method for sensing and classifying olfactory products is provided. The method comprising: receiving, by an electronic sensing system, a olfactory product; detecting and extracting, using a sensing module of the electronic sensing system, one or more smell characteristics of the olfactory product by identifying a headspace of the olfactory product; performing, by using a comparison module, a comparison of the one or more extracted smell characteristics of the olfactory product with smell characteristics associated with a historic training data stored in a database; and generating based on the comparison, by one or more neural network models, by using a report generation module, a report for the olfactory product comprising at least one of type of the olfactory product, name of the olfactory product, a status of the olfactory product, an age of the olfactory product, and a decaying index. In an embodiment, the status of the olfactory product comprises at least one of consumable, and non-consumable. In an embodiment of the present disclosure, at least one of freshness characteristic and stale characteristic of the olfactory product is determined based on the decaying index.

In an embodiment of the present disclosure, the step of performing a comparison of the one or more extracted smell characteristics of the olfactory product with smell characteristics associated with a historic training data stored in a database comprises: analyzing the extracted smell characteristics of the olfactory product to obtain a set of normalized values and intensity values; performing a comparison of the set of normalized values and the intensity values with values associated with the historic training data stored in the database; and determining, using one or more neural network models, a match between the at least some of values from the set of normalized values and intensity values with the values with the historic training data stored in the database.

In an embodiment of the present disclosure, the method may further comprise classifying, using a classification module, the olfactory product into one or more categories based on at least one of the generated report and the historic training data.

In an embodiment, the step of receiving an olfactory product is preceded by: training the electronic sensing system based on the historic training data comprising: receiving one or more olfactory products; extracting one or more smell characteristics of the one or more olfactory products; generating one or more reports pertaining to the one or more olfactory products; and classifying the one or more olfactory products into one or more categories.

In another embodiment, an electronic sensing system for sensing and classifying olfactory products is provided. The system comprising: one or more processors; and one or more internal data storage devices operatively coupled to the one or more processors for storing instructions configured for execution by the one or more processors, the instructions being comprised in: a sensing module that is configured to receive an olfactory product, and detect and extract one or more smell characteristics of the olfactory product by identifying a headspace of the olfactory product; a comparison module configured to perform a comparison of the one or more extracted smell characteristics of the olfactory product with one or more smell characteristics associated with a historic training data stored in a database; and a report generation module configured to generate, based on the comparison, using the one or more neural network models, a report for the olfactory product comprising at least one of type of the consumable, name of the olfactory product, a status of the olfactory product, an age of the olfactory product, and a decaying index. In an embodiment, the status of the olfactory product comprises at least one of consumable, and non-consumable. In an embodiment, the decaying index is indicative at least one of freshness characteristic and stale characteristic of the olfactory product.

The electronic sensing system may further comprise a classification module that is configured to classify, using one or more classifiers, the olfactory product into one or more categories based on the generated report and the historic training data.

In an embodiment, the step of receiving an olfactory product is preceded by: training the electronic sensing system based on the historic training data comprising: receiving one or more olfactory products; detecting and extracting one or more smell characteristics of the one or more olfactory products; generating one or more reports pertaining to the one or more olfactory products; and classifying the one or more olfactory products into one or more categories.

In an embodiment of the present disclosure, the one or more extracted smell characteristics of the olfactory product are compared with smell characteristics associated with a historic training data stored in the database by: analyzing the extracted smell characteristics of the olfactory product to obtain a set of normalized values and intensity values; performing a comparison of the set of normalized values and the intensity values with values associated with the historic training data stored in the database; and determining, using one or more neural network models, a match between the at least some of values from the set of normalized values and intensity values with the values with the historic training data stored in the database.

In yet another aspect, one or more non-transitory machine readable information storage mediums comprising one or more instructions is provided. The one or more instructions which when executed by one or more hardware processors causes receiving, by an electronic sensing system, a olfactory product; detecting and extracting, using a sensing module of the electronic sensing system, one or more smell characteristics of the olfactory product by identifying a headspace of the olfactory product; performing, by using a comparison module, a comparison of the one or more extracted smell characteristics of the olfactory product with smell characteristics associated with a historic training data stored in a database; and generating based on the comparison, by one or more neural network models, by using a report generation module, a report for the olfactory product comprising at least one of type of the olfactory product, name of the olfactory product, a status of the olfactory product, an age of the olfactory product, and a decaying index. In an embodiment, the status of the olfactory product comprises at least one of consumable, and non-consumable. In an embodiment of the present disclosure, at least one of freshness characteristic and stale characteristic of the olfactory product is determined based on the decaying index.

In an embodiment of the present disclosure, the step of performing a comparison of the one or more extracted smell characteristics of the olfactory product with smell characteristics associated with a historic training data stored in a database comprises: analyzing the extracted smell characteristics of the olfactory product to obtain a set of normalized values and intensity values; performing a comparison of the set of normalized values and the intensity values with values associated with the historic training data stored in the database; and determining, using one or more neural network models, a match between the at least some of values from the set of normalized values and intensity values with the values with the historic training data stored in the database.

In an embodiment of the present disclosure, the instructions when further executed by the one or more processors may cause classifying, using a classification module, the olfactory product into one or more categories based on at least one of the generated report and the historic training data.

In an embodiment, the step of receiving an olfactory product is preceded by: training the electronic sensing system based on the historic training data comprising: receiving one or more olfactory products; extracting one or more smell characteristics of the one or more olfactory products; generating one or more reports pertaining to the one or more olfactory products; and classifying the one or more olfactory products into one or more categories.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Referring now to the drawings, and more particularly to FIGS. 1 through 5, where similar reference characters denote corresponding features consistently throughout the figures, there are shown preferred embodiments and these embodiments are described in the context of the following exemplary system and/or method.

Figure 1:
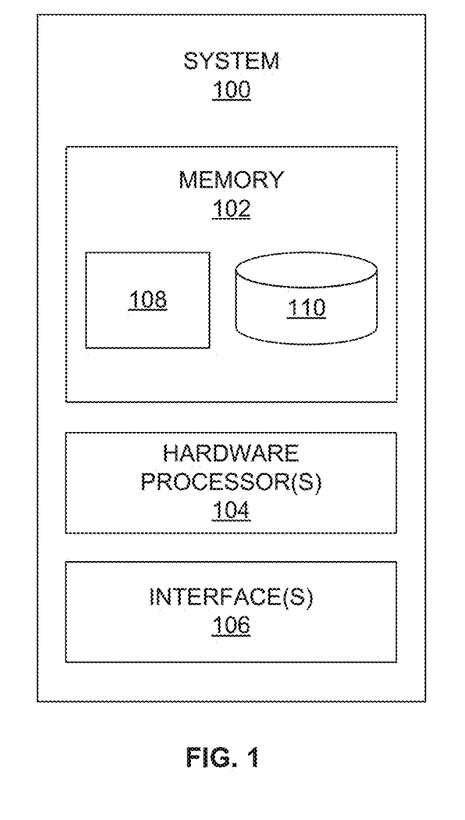
FIG. 1 illustrates an exemplary block diagram of a system for sensing and classifying olfactory products according to an embodiment of the present disclosure.

FIG. 1 illustrates an exemplary block diagram of a system 100 for sensing and classifying olfactory products according to an embodiment of the present disclosure. In an embodiment of the present disclosure, the system 100 may also be referred herein as 'an electronic sensing system' or 'an electronic sensing and classification system'. In an embodiment, the system 100 includes one or more processors 104, communication interface device(s) or input/output (I/O) interface(s) 106, and one or more data storage devices or memory 102 operatively coupled to the one or more processors 104. The memory 102 comprises one or more modules 108 and a database 110. The one or more processors 104 may be one or more software processing modules and/or hardware processors. In an embodiment, the hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, one or more modules (not shown) of the system 100 can be stored in the memory 102.

Figure 2:
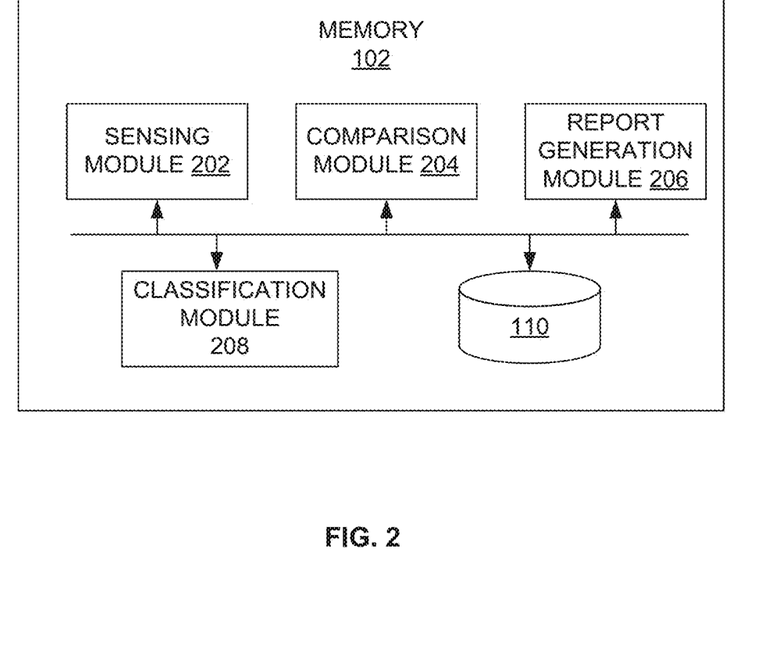
FIG. 2 is a block diagram of various modules stored in a memory of the electronic sensing system of FIG. 1 in accordance with an embodiment of the present disclosure.

FIG. 2, with reference to FIG. 1, is a block diagram of various modules stored in the memory 102 of the electronic sensing system 100 of FIG. 1 in accordance with an embodiment of the present disclosure. In an embodiment of the present disclosure, the memory 102 comprises a sensing module 202, a comparison module 204, a report generation module 206, a classification module 208, and the database 110. In an embodiment of the present disclosure, the sensing module 202, the comparison module 204, the report generation module 206, and the classification module 208 are implemented as at least one of a logically self-contained part of a software program, a self-contained hardware component, and/or, a self-contained hardware component with a logically self-contained part of a software program embedded into each of the hardware component that when executed perform the above method described herein.

Figure 3:
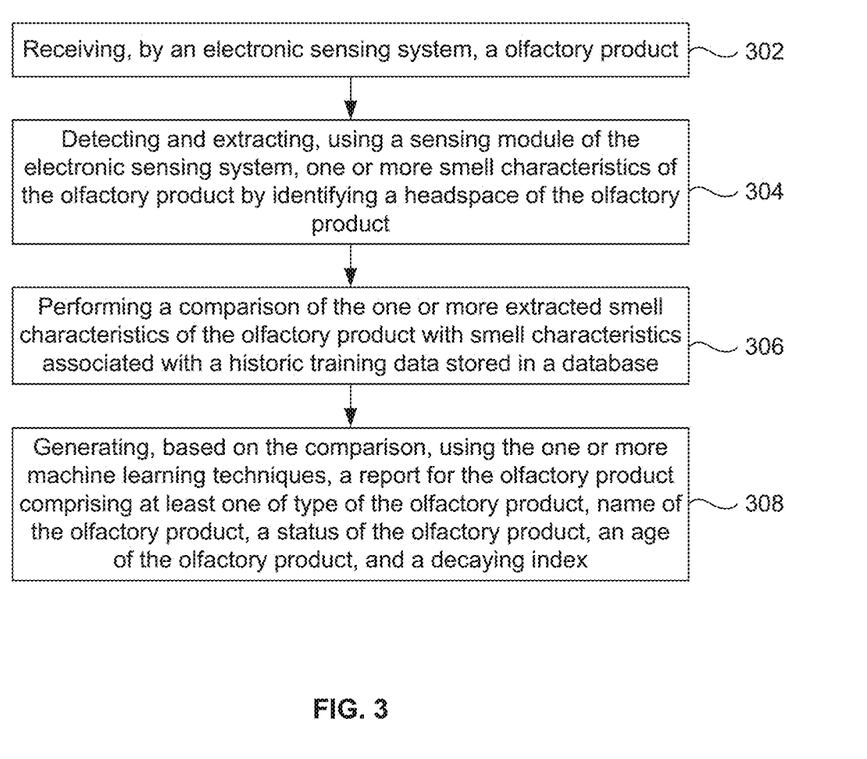
FIG. 3 illustrates an exemplary flow diagram of a method for sensing and classifying olfactory products using the system of FIG. 1 in accordance with an embodiment of the present disclosure.

FIG. 3, with reference to FIGS. 1-2, illustrates an exemplary flow diagram of a method for sensing and classifying olfactory products using the system 100 of FIG. 1 in accordance with an embodiment of the present disclosure. In an embodiment, the system 100 comprises one or more data storage devices or the memory 102 operatively coupled to the one or more hardware processors 104 and is configured to store instructions for execution of steps of the method by the one or more processors 104. The steps of the method of the present disclosure will now be explained with reference to the components of the system 100 and the modules 202-208 as depicted in FIGS. 1-2, and the flow diagram. In an embodiment of the present disclosure, the system 100 may be trained based on historic training data, wherein the system 100 is trained by receiving one or more olfactory products, extracting one or more detected smell characteristics of the one or more olfactory products, generating one or more reports pertaining to the one or more olfactory products, and further classifying the one or more olfactory products into one or more categories. The smell characteristics are detected and further analyzed to generate normalized values and intensity values. The smell characteristics (e.g., gaseous attributes) of the olfactory products, and the generated normalized values and the intensity values thereof are mapped against each other and stored in the database 110. The above step of training is performed for generating report(s) for and classifying subsequent olfactory product(s). The steps of training as described above generate output(s) which may be stored in the form of 'historic training data' in the database 210 of the memory 102, and the database may be dynamically updated with attributes associated with the smell characteristics of the olfactory products.

When the system 100 is undergoing (and/or undergoes) the training with the implementation (or integration) of one or more neural network model(s), the system 100 is configured to detect the smell characteristics using the sensing module 202. In an embodiment of the present disclosure, the one or more neural network models may be stored in the memory 102 and executed on the system 100 to enable and train the system 100 for sensing and classifying olfactory products. In an embodiment of the present disclosure the neural network models (e.g., deep belief network(s)—DBNs) may implement supervised learning technique and/or unsupervised learning technique for training and learning the pattern of detecting, sensing and classifying olfactory products. The sensing module 202 as described above may comprise an array of one or more sensors (e.g., olfactory sensors) that sense the smell characteristics. In this process, the one or more integrated neural network models also get trained which enable the system 100 to generate report(s) and classify the olfactory products into one or more categories in an efficient (or improved) manner. The one or more trained neural network models may rely on historic training data that includes historic normalized values, historic intensity values, and the historic smell characteristics of the olfactory products (which are previously received and analyzed). The trained neural network models may map (i) the smell characteristics and (ii) the historic normalized values and the historic intensity values to (i) specific type of the olfactory product, (ii) name of the olfactory product, (iii) a status of the olfactory product, (iv) age of the olfactory product, and (v) a decaying index being computed. In some scenario upon such mappings, one or more users of the system 100 may provide one or more inputs (e.g., suggestions, corrections to the mapped data) and these inputs may be considered by the trained neural network models to store corrected and suggested inputs against each olfactory product. Based on the inputs provided by the one or more users, the system 100 and the trained neural network models learn the pattern of the inputs, and provides recommendations or generates report(s) for subsequent olfactory products.

Referring back to the steps of FIG. 3, in an embodiment of the present disclosure, at step 302, the electronic sensing system 100 receives an olfactory product. In an embodiment of the present disclosure, the electronic sensing system 100 comprises the sensing module 202 (also referred as 'smell chamber' or 'sensor array') that receives the olfactory product. In an embodiment of the present disclosure, at step 304, the one or more processors 104 detect and extract, using the sensing module 202 of the electronic sensing system 100, one or more smell characteristics of the olfactory product by identifying a headspace of the olfactory product. In an embodiment of the present disclosure, at step 306, the one or more processors 104 perform a comparison (e.g., using the comparison module 204) of the one or more extracted smell characteristics of the olfactory product with one or more smell characteristics associated with a historic training data (also referred as 'reference data' or 'reference training data') stored in the database 210. In an embodiment of the present disclosure, the step of performing a comparison (e.g., using the comparison module 204) of the one or more extracted smell characteristics of the olfactory product with one or more smell characteristics associated with the historic training data stored in the database 210 comprises analyzing the extracted smell characteristics of the olfactory product to obtain (or generate) a set of normalized values and intensity values, wherein the set of normalized values are obtained (or generated) by converting the extracted smell characteristics to machine readable (understandable) format and then normalizing the machine readable format to obtain the set of normalized values. In some scenarios of the present disclosure, the smell characteristics of a given olfactory product may be directly analyzed and normalized to obtain the set of normalized values. Similarly, the intensity values may be obtained based on the detected (or extracted) smell characteristics of the olfactory product.

Below are illustrative examples of extracted smell characteristics by the sensing module 202 (or the array of one or more sensors) that are converted to machine or system readable (or understandable) format as described below in Table 1 by way of example:

| Values from the sensing module 202 (or array of sensors) | | | |
|---|---|---|---|
| 1.25 | 2.3 | 1.17 | 0.87 |
| 1.25 | 2.3 | 1.17 | 0.87 |
| 1.25 | 2.3 | 1.17 | 0.87 |
| 1.25 | 2.3 | 1.17 | 0.87 |
| 1.25 | 2.3 | 1.17 | 0.87 |
| 1.25 | 2.3 | 1.17 | 0.87 |

Table 1

1.25 may represent an output derived from a first sensor. Similarly, 2.3 may represent an output derived from a second sensor. Similarly, 1.17 may represent an output derived from a third sensor. Similarly, 0.87 may represent an output derived from a fourth sensor. The above smell characteristics (e.g., the machine readable format data of Table 1) may be analyzed by the sensing module 202 to obtain a set of normalized values and intensity values.

The step of performing comparison further includes performing a comparison of the set of normalized values and the intensity values with values (e.g., historic normalized values, and historic intensity values) associated with the historic training data stored in the database 110. The system 100 may further determine a match between the at least some of values from the set of normalized values and intensity values with the values with the historic training data stored in the database is determined. In an embodiment of the present disclosure, the comparison module 204 may invoke the one or more trained neural network model(s) (or the comparison module 204 may be integrated with the one or more neural network model(s)) to determine a match between the one or more extracted smell characteristics of the olfactory product and the one or more smell characteristics associated with the historic training data. More specifically, the system 100 may be integrated with the one or more neural network models that are trained using the historic training data stored in the database 110, to perform a comparison of the set of normalized values and the intensity values with values (e.g., historic normalized values, and historic intensity values) associated with the historic training data stored in the database, and using the one or more trained neural network model(s), a match (e.g., a full match, or at least a partial match, or a minimum distance, or a minimum difference) may be determined between the at least some of values from the set of normalized values and intensity values with the values with the historic training data stored in the database 110.

In an embodiment of the present disclosure, at step 208, the processors 104 generate, (using the one or more trained neural network models or the report generation module 206), a report for the olfactory product comprising at least one of type of the olfactory product, name of the olfactory product, a status of the olfactory product, an age of the olfactory product, and a decaying index. In an embodiment, based on the comparison (and/or the level of match or difference or distance (e.g., minimum difference or minimum distance between (i) the normalized values, and intensity values and (ii) historic normalized values and intensity values), the one or more trained neural network models (and/or the report generation module 206) generate the report as mentioned above. In an embodiment, the system 100 may generate the report based on the minimum difference or minimum distance between (i) the smell characteristics of the given olfactory product and (ii) historic smell characteristics stored in the database 110.

The above steps and embodiments of the present disclosure may be better understood by way of below example:

When an olfactory product is received, smell characteristic of the olfactory product are detected and extracted. The extracted smell characteristics may be analyzed and normalized by the smell chamber (or the sensing module 202) of the system 100 and normalized values pertaining to detected smell characteristics are obtained (or generated). Similarly, based on the detected (or extracted) smell characteristics of the olfactory product, the sensing module 202 generates intensity value(s) (e.g., quality) pertaining to the olfactory product. The system 100 may generate a report (or a graphical representation) of the normalized values against the intensity values of the olfactory product. In an embodiment of the present disclosure, the normalized values and the intensity values are obtained in real time when the sensing module 202 detects and extracts smell characteristics of the olfactory product. In an embodiment of the present disclosure the normalized values and the intensity values may be referred as 'real time values'. The system 100 may then calculate distance (e.g., a difference) between these real time values obtained from the sensing module 202 and values of smell characteristics from the historic training data stored in the database. In an embodiment of the present disclosure, the comparison module 204 compares the real time values with the values (historic training data) stored in the database. The distance of (i) real time values (e.g., current normalized values and intensity values) and (ii) the values (e.g., historic normalized values and historic intensity values) from the historic training data that results in a match (or close match or a minimum distance match or minimum difference or full match, or partial match) determines the smell of the olfactory product. Based on output of the match, the system 100 (or the report generation module 206 or the one or more trained neural network models) generates a report pertaining to the olfactory product. The method further comprises classifying, using the classification module 208, the olfactory product into one or more categories based on at least one of the generated report and the historic training data. In an embodiment of the present disclosure, the classification module 208 may invoke one or more classifiers (stored in the memory 102) that are executed on the system 100 which are configured to classify the olfactory product into the one or more categories. In an embodiment of the present disclosure, the one or more classifiers comprise but are not limited to, one or more Linear classifiers (e.g., Fisher's linear discriminant, Logistic regression, Naive Bayes classifier, Perceptron, etc.), Support Vector Machines (SVM) (e.g., Least squares support vector machines), Quadratic classifiers, Kernel estimation (e.g., k-nearest neighbor), Decision trees, Random forests, Neural networks, Learning vector quantization, etc.

Figure 4:
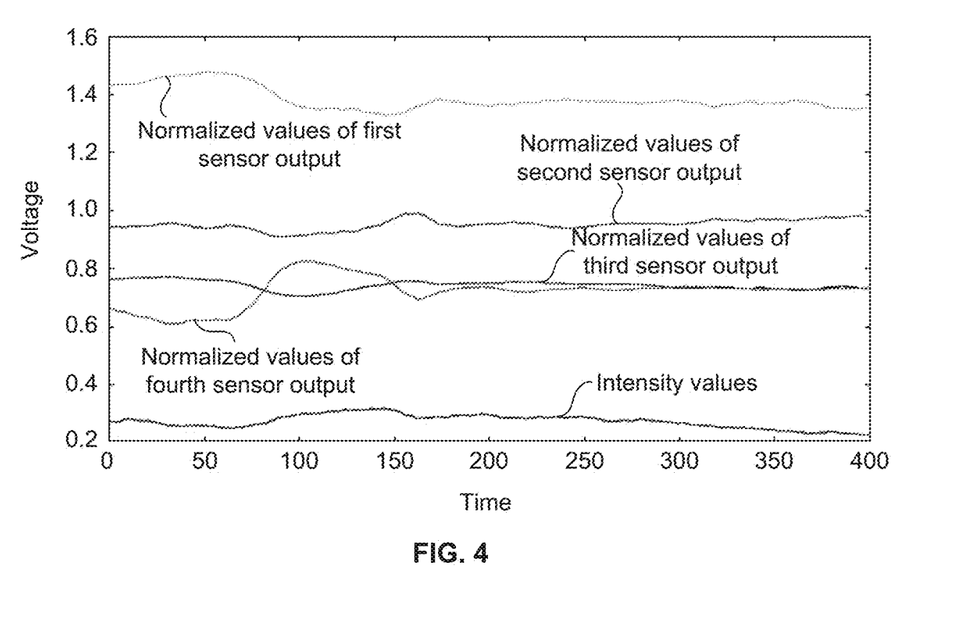
FIG. 4 illustrates an exemplary graphical representation of normalized values and intensity values with respect to voltage and time in accordance with an embodiment of the present disclosure.

When a new olfactory product is received by the system 100, the system 100 or the sensors detect smell characteristics, which are converted to machine readable format (or any format) that is readable or understandable by the trained neural network models to generate normalized values and intensity values for the given new olfactory product. These normalized values and intensity values may be used to generate a graphical representation. FIG. 4, with reference to FIGS. 1-3, illustrates an exemplary graphical representation of normalized values and intensity values with respect to voltage and time (e.g., in milliseconds) in accordance with an embodiment of the present disclosure. More specifically, FIG. 4 depicts an exemplary graphical representation of normalized values of the output derived from the one or more sensors (or the sensing module 202) and intensity value thereof with respect to voltage and time.

In an embodiment of the present disclosure, the status of the olfactory product comprises at least one of consumable, and non-consumable. In an embodiment of the present disclosure, the processors 104 perform a comparison of the decaying index with a threshold index and determine at least one of freshness characteristic and stale characteristic of the olfactory product based on the comparison. In an embodiment, the threshold index (also referred as pre-defined threshold index is either set (or defined) by the system 100 or is configurable by a user. In an embodiment, the threshold index may be dynamic and may change based on the training level and learning pattern of the system 100 which act as a continuous feedback for subsequent sensing and classification of olfactory products (e.g., new feeds) to provide accurate (or near accurate output(s)). The continuous feedback may also help the system 100 (or the neural network models) to adapt and predict the nature, days, peak odour levels, and type of the olfactory products and unlearn negative learning characteristics.

Figure 5:
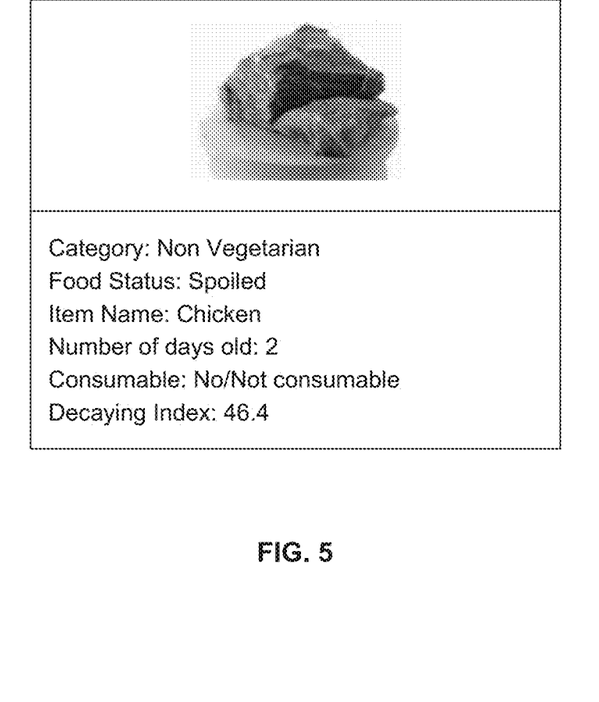
FIG. 5 illustrates an exemplary user interface view depicting a report pertaining to an olfactory product in accordance with an embodiment of the present disclosure.

FIG. 5, with reference to FIGS. 1-4, illustrates an exemplary user interface view depicting a report pertaining to an olfactory product in accordance with an embodiment of the present disclosure. More specifically, FIG. 3 illustrates an exemplary report generated by the system 100 of FIG. 1 depicting the type of the olfactory product (e.g., food item), name of the olfactory product (e.g., chicken or meat product), a status of the olfactory product (e.g., spoiled), an age of the olfactory product (e.g., 2 days old), and a decaying index (e.g., 46.4) which is an indicative of the freshness or stale characteristic of the olfactory product. In an embodiment of the present disclosure, the decaying index may be computed using an expression provided below by way of example:

$$\text{Rate of decay (decaying index)} = \lim_{t \to 0} \frac{f(x + \Delta t - f(x))}{\Delta t}, \quad (1)$$

where f(x+Δt) is decay at time (t+Δt), and f(x) is decay at time (t) and denotes the freshness value at time (t), and Δ (delta) is an increment in the value of time.

Given data from 'N' sensors, the values are fed into the trained system 100. The system 100 gives a label as the output which indicates the level of decay and what kind/type of substance/product it is. For example: a value '5' may denote chicken on its 2nd level of freshness. These values may be monitored over a time and then the expression (1) above is applied on a time period. Over this time period the rate of decay is calculated. Therefore, the value 46.4 is the difference in freshness in a time interval devised by the time interval itself. The age of the product may be a direct inference from the output of the one or more trained neural network models based on the historic training data. The non-linearity of the one or more neural network models using which the index is calculated is explained by way of an exemplary expression (2) as depicted below:

$$\text{Labelling} = \text{activation} \frac{e^{x_i}}{\sum_{i=1}^{n} e^{x_i}}; x_i = w_i t + b, \quad (2)$$

where 'w' is weight learnt by the system 100 and 'b' is bias towards each of the classes (or the one or more categories) wherein 'w' and 'b' are the parameters updated by the neural network models, and 'e' is exponential wherein total exponential is a calculation of probability. The output of the above expression (2) may be used to represent a categorical distribution, which is, a probability distribution over 'n' different possible outcomes. In an embodiment of the present disclosure, the system 100 may choose (or select) activation function for a slave network among the neural network models to learn an incoming input dataset pertaining to olfactory products. The system 100 may modify the structure of the network (neural network model(s)) as per the requirement, and if weights going from a node is null then the structure may be redefined.

The embodiments of the present disclosure provide electronic sensing systems and methods for sensing and classifying olfactory products. The system 100 is configured to generate signal pattern that are used for characterizing odors (or smell) by using headspace sampling, sensor array, and pattern recognition modules. Unlike conventional systems, the embodiments of the present disclosure enables integration of the system 100 with Internet of Things (IoT) to provide better results (or outcomes) in the field of food industrial management and personal health management, which intelligently senses olfactory products (e.g., food items, and the like) and classifies them in one or more categories (e.g., vegetarian, non-vegetarian, fruit, organic, inorganic, and the like). Unlike conventional systems where they fail to identify the quality of the olfactory products, the system 100 implements neural network model(s) to identify intensity (e.g., quality) of the olfactory products thereby even predicting how many days the product is old, whether it is consumable or not, and provides statistical data (or report) pertaining to the olfactory product (e.g., the food item). With the neural network models integrated with the system 100, the embodiments of the present disclosure enable the system 100 to dynamically learn the sensing and classification/categorization patterns and provide or generate optimized (or accurate or near accurate) report(s) for a given olfactory product based on the historic training data. The integration of the system 100 with neural network model(s) enables computation of age of the olfactory products, and decaying index thus determining the freshness and/or stale characteristics of the olfactory products.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:
1. A processor implemented method, comprising:
receiving, by an electronic sensing system (100), a olfactory product (302);
detecting and extracting, using a sensing module (202) of the electronic sensing system (100), one or more smell characteristics of the olfactory product by identifying a headspace of the olfactory product (304);
performing, by using a comparison module (204), a comparison of the one or more extracted smell characteristics of the olfactory product with smell characteristics associated with a historic training data stored in a database (306), wherein the database is dynamically updated with attributes associated with the one or more smell characteristics of the olfactory product;
generating based on the comparison, by one or more neural network models, by using a report generation module (206), a report for the olfactory product comprising type of the olfactory product, name of the olfactory product, a status of the olfactory product, an age of the olfactory product, and a decaying index (308), wherein the decaying index is computed based on a rate of decay of the olfactory product over a time period, wherein at least one of freshness characteristic and stale characteristic of the olfactory product is determined based on the decaying index, wherein an output of one or more neural network models is calculated with an expression of:

$$\text{labelling} = \text{activation } \frac{e^{x_i}}{\sum_{i=1}^{n} e^{x\_i}}; x_i = w_i t + b$$

where 'w' is a weight and 'b' is bias towards each of the classes, and 'e' is exponential wherein total exponential is a calculation of probability,
wherein the report is generated based on a minimum distance between the one or more extracted smell characteristics of the olfactory product and the smell characteristics associated with the historic training data stored in the database,
wherein the step of receiving an olfactory product is preceded by:
training the electronic sensing system based on the historic training data comprising:
receiving one or more olfactory products, extracting one or more smell characteristics of the one or more olfactory products, generating one or more reports pertaining to the one or more olfactory products and classifying the one or more olfactory products into one or more categories.
2. The processor implemented method of claim 1, wherein the step of performing a comparison of the one or more extracted smell characteristics of the olfactory product with smell characteristics associated with a historic training data stored in a database comprises:
analyzing the extracted smell characteristics of the olfactory product to obtain a set of normalized values and intensity values;

performing a comparison of the set of normalized values and the intensity values with values associated with the historic training data stored in the database; and determining, using one or more neural network models, a match between the at least some of values from the set of normalized values and intensity values with the values with the historic training data stored in the database.

3. The processor implemented method of claim 1, further comprising classifying, using a classification module (208), the olfactory product into the one or more categories based on at least one of the generated report and the historic training data.

4. The processor implemented method of claim 1, wherein the step of receiving an olfactory product is preceded by: training the electronic sensing system based on the historic training data comprising:
receiving one or more olfactory products;
extracting one or more smell characteristics of the one or more olfactory products;
generating one or more reports pertaining to the one or more olfactory products; and
classifying the one or more olfactory products into the one or more categories.

5. The processor implemented method of claim 1, wherein the status of the olfactory product comprises at least one of consumable, and non-consumable.

6. An electronic sensing system comprising:
one or more processors (104); and
one or more internal data storage devices (102) operatively coupled to the one or more processors (104) and storing instructions configured for execution by the one or more processors (104), the instructions comprises:
a sensing module (202) that is configured to receive an olfactory product, and detect and extract one or more smell characteristics of the olfactory product by identifying a headspace of the olfactory product;
a comparison module (204) configured to perform a comparison of the one or more extracted smell characteristics of the olfactory product with one or more smell characteristics associated with a historic training data stored in a database, wherein the database is dynamically updated with attributes associated with the one or more smell characteristics of the olfactory product;
a report generation module (206) configured to generate, based on the comparison, using the one or more neural network models, a report for the olfactory product comprising at type of the olfactory product, name of the olfactory product, a status of the olfactory product, an age of the olfactory product, and a decaying index, wherein the decaying index is computed based on a rate of decay of the olfactory product over a time period, wherein at least one of freshness characteristic and stale characteristic of the olfactory product is determined based on the decaying index, wherein an output of one or more neural network models is calculated with an expression of:

$$\text{labelling} = \text{activation} \frac{e^{x_i}}{\sum_{i=1}^{n} e^{x\_i}}; x_i = w_i t + b$$

where 'w' is a weight and 'b' is bias towards each of the classes, and 'e' is exponential wherein total exponential is a calculation of probability,
wherein the report is generated based on a minimum distance between the one or more extracted smell characteristics of the olfactory product and the smell characteristics associated with the historic training data stored in the database,
wherein the step of receiving an olfactory product is preceded by:
training the electronic sensing system based on the historic training data comprising:
receiving one or more olfactory products, extracting one or more smell characteristics of the one or more olfactory products, generating one or more reports pertaining to the one or more olfactory products and classifying the one or more olfactory products into one or more categories.

7. The electronic sensing system of claim 6, further comprising a classification module (208), that is configured to classify, using one or more classifiers, the olfactory product into the one or more categories based on the generated report and the historic training data.

8. The electronic sensing system of claim 6, wherein the step of receiving an olfactory product is preceded by: training the electronic sensing system based on the historic training data comprising:
receiving one or more olfactory products;
detecting and extracting one or more smell characteristics of the one or more olfactory products;
generating one or more reports pertaining to the one or more olfactory products; and
classifying the one or more olfactory products into the one or more categories.

9. The electronic sensing system of claim 6, wherein the status of the olfactory product comprises at least one of consumable, and non-consumable.

10. The electronic sensing system of claim 6, wherein the one or more extracted smell characteristics of the olfactory product are compared with smell characteristics associated with a historic training data stored in the database by:
analyzing the extracted smell characteristics of the olfactory product to obtain a set of normalized values and intensity values;
performing a comparison of the set of normalized values and the intensity values with values associated with the historic training data stored in the database; and
determining, using one or more neural network models, a match between the at least some of values from the set of normalized values and intensity values with the values with the historic training data stored in the database.

11. One or more non-transitory machine readable information storage mediums comprising one or more instructions which when executed by one or more hardware processors cause;
receiving, by an electronic sensing system, a olfactory product;
detecting and extracting, one or more smell characteristics of the olfactory product by identifying a headspace of the olfactory product;
performing, a comparison of the one or more extracted smell characteristics of the olfactory product with smell characteristics associated with a historic training data stored in a database, wherein the database is dynamically updated with attributes associated with the one or more smell characteristics of the olfactory product;

generating based on the comparison, by one or more neural network models, a report for the olfactory product comprising type of the olfactory product, name of the olfactory product, a status of the olfactory product, an age of the olfactory product, and a decaying index, wherein the decaying index is computed based on a rate of decay of the olfactory product over a time period, wherein at least one of freshness characteristic and stale characteristic of the olfactory product is determined based on the decaying index, wherein an output of one or more neural network models is calculated with an expression of:

$$\text{labelling} = \text{activation} \frac{e^{x_i}}{\sum_{i=1}^{n} e^{x\_i}}; x_i = w_i t + b$$

where 'w' is a weight and 'b' is bias towards each of the classes, and 'e' is exponential wherein total exponential is a calculation of probability, wherein the report is generated based on a minimum distance between the one or more extracted smell characteristics of the olfactory product and the smell characteristics associated with the historic training data stored in the database, wherein the step of receiving an olfactory product is preceded by:

training the electronic sensing system based on the historic training data comprising:

receiving one or more olfactory products, extracting one or more smell characteristics of the one or more olfactory products, generating one or more reports pertaining to the one or more olfactory products and classifying the one or more olfactory products into one or more categories.

12. The one or more non-transitory machine readable information storage mediums of claim 11, wherein the step of performing a comparison of the one or more extracted smell characteristics of the olfactory product with smell characteristics associated with a historic training data stored in a database comprises:

analyzing the extracted smell characteristics of the olfactory product to obtain a set of normalized values and intensity values;

performing a comparison of the set of normalized values and the intensity values with values associated with the historic training data stored in the database; and determining, using one or more neural network models, a match between the at least some of values from the set of normalized values and intensity values with the values with the historic training data stored in the database.

13. The one or more non-transitory machine readable information storage mediums of claim 11, wherein the one or more instructions further cause classifying the olfactory product into the one or more categories based on at least one of the generated report and the historic training data.

14. The one or more non-transitory machine readable information storage mediums of claim 11, wherein the step of receiving an olfactory product is preceded by:

training the electronic sensing system based on the historic training data comprising:

receiving one or more olfactory products;

extracting one or more smell characteristics of the one or more olfactory products;

generating one or more reports pertaining to the one or more olfactory products; and classifying the one or more olfactory products into the one or more categories.

15. The one or more non-transitory machine readable information storage mediums of claim 11, wherein the status of the olfactory product comprises at least one of consumable, and non-consumable.

* * * * *